(12) United States Patent
Boyle et al.

(10) Patent No.: US 7,241,304 B2
(45) Date of Patent: Jul. 10, 2007

(54) FLEXIBLE AND CONFORMABLE EMBOLIC FILTERING DEVICES

(75) Inventors: William J. Boyle, Fallbrook, CA (US); Benjamin C. Huter, Murrieta, CA (US); Scott J. Huter, Temecula, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 326 days.

(21) Appl. No.: 10/027,915

(22) Filed: Dec. 21, 2001

(65) Prior Publication Data

US 2003/0120303 A1    Jun. 26, 2003

(51) Int. Cl.
*A61M 29/00* (2006.01)
(52) U.S. Cl. .................. 606/200; 604/96.01
(58) Field of Classification Search ............. 606/200, 606/194, 114, 192, 127, 128, 159, 191; 604/96, 604/96.01, 104, 106, 107, 108, 109
See application file for complete search history.

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | 5/1987 | DiPisa, Jr. | |
| 4,688,553 A | 8/1987 | Metals | |
| 4,706,671 A | 11/1987 | Weinrib | |

(Continued)

FOREIGN PATENT DOCUMENTS

EP     0427429 A3     9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74.

*Primary Examiner*—Michael J. Hayes
*Assistant Examiner*—Victor X. Nguyen
(74) *Attorney, Agent, or Firm*—Fulwider Patton LLP

(57) ABSTRACT

A self-expanding cage for use in conjunction with an embolic filtering device includes one or more circumferential members adapted to expand from an unexpanded position to a expanded position within the patient's body vessel. At least one proximal strut and at least one distal strut are attached to the circumferential member to form the basket. The circumferential member may include a plurality of bending regions which enhance the ability of the circumferential member to move between the unexpanded and expanded positions. The proximal and distal struts can be attached to one of the bending regions. When two or more circumferential members are utilized, each member may be connected by a connecting strut which may be connected at a bending region. The connecting strut can be a straight segment or may have a non-linear shape to provide additional flexibility. The expandable cage can be mounted to a elongated member, such as a guide wire, and can be either permanently mounted or rotatably mounted thereto.

25 Claims, 6 Drawing Sheets

U.S. PATENT DOCUMENTS

| | | | |
|---|---|---|---|
| 4,723,549 A | 2/1988 | Wholey et al. | |
| 4,727,873 A | 3/1988 | Mobin-Uddin | |
| 4,781,177 A | 11/1988 | Lebigot | |
| 4,790,812 A | 12/1988 | Hawkins, Jr. et al. | |
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |
| 4,990,156 A | 2/1991 | Lefebvre | |
| 4,997,435 A | 3/1991 | Demeter | |
| 4,998,539 A | 3/1991 | Delsanti | |
| 5,053,008 A | 10/1991 | Bajaj | |
| 5,064,428 A | 11/1991 | Cope et al. | |
| 5,071,407 A | 12/1991 | Termin et al. | |
| 5,092,839 A | 3/1992 | Kipperman | |
| 5,100,423 A * | 3/1992 | Fearnot | 606/159 |
| 5,100,425 A | 3/1992 | Fischell et al. | |
| 5,102,415 A | 4/1992 | Guenther et al. | |
| 5,108,419 A | 4/1992 | Reger et al. | |
| 5,152,777 A | 10/1992 | Goldberg et al. | |
| 5,158,548 A | 10/1992 | Lau | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,383,887 A | 1/1995 | Nadal | |
| 5,421,832 A | 6/1995 | Lefebvre | |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,658,296 A | 8/1997 | Bates et al. | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,776,162 A | 7/1998 | Kleshinski | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maas | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,935,139 A | 8/1999 | Bates | |
| 5,941,869 A | 8/1999 | Patterson et al. | |
| 5,941,896 A | 8/1999 | Kerr | |
| 5,944,728 A | 8/1999 | Bates | |
| 5,954,745 A | 9/1999 | Gertler et al. | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,013,093 A | 1/2000 | Nott et al. | |
| 6,022,336 A | 2/2000 | Zadno-Azizi et al. | |
| 6,027,520 A | 2/2000 | Tsugita et al. | |
| 6,042,598 A | 3/2000 | Tsugita et al. | |
| 6,051,015 A | 4/2000 | Maahs | |
| 6,053,932 A | 4/2000 | Daniel et al. | |
| 6,059,814 A | 5/2000 | Ladd | |
| 6,066,158 A | 5/2000 | Engelson et al. | |
| 6,074,357 A | 6/2000 | Kaganov et al. | |
| 6,086,605 A | 7/2000 | Barbut et al. | |
| 6,090,097 A | 7/2000 | Barbut et al. | |
| 6,096,053 A | 8/2000 | Bates | |
| 6,099,534 A | 8/2000 | Bates et al. | |
| 6,099,549 A | 8/2000 | Bosma et al. | |
| 6,117,154 A | 9/2000 | Barbut et al. | |
| 6,129,739 A | 10/2000 | Khosravi | |
| 6,136,015 A | 10/2000 | Kurz | |
| 6,136,016 A | 10/2000 | Barbut et al. | |
| 6,142,987 A | 11/2000 | Tsugita | |
| 6,152,946 A | 11/2000 | Broome et al. | |
| 6,152,947 A | 11/2000 | Ambrisco et al. | |
| 6,165,198 A | 12/2000 | McGurk et al. | |
| 6,165,200 A | 12/2000 | Tsugita et al. | |
| 6,168,579 B1 | 1/2001 | Tsugita et al. | |
| 6,168,604 B1 | 1/2001 | Cano | |
| 6,171,327 B1 | 1/2001 | Daniel et al. | |
| 6,171,328 B1 | 1/2001 | Addis | |
| 6,174,318 B1 | 1/2001 | Bates et al. | |
| 6,176,849 B1 | 1/2001 | Yang et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,224,620 B1 | 5/2001 | Maahs | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,251,122 B1 | 6/2001 | Tsukernik | |
| 6,254,633 B1 | 7/2001 | Pinchuk et al. | |
| 6,258,115 B1 | 7/2001 | Dubrul | |
| 6,258,120 B1 | 7/2001 | McKenzie et al. | |
| 6,264,663 B1 | 7/2001 | Cano | |
| 6,264,672 B1 | 7/2001 | Fisher | |
| 6,267,776 B1 | 7/2001 | O'Connell | |
| 6,267,777 B1 | 7/2001 | Bosma et al. | |
| 6,270,477 B1 | 8/2001 | Bagaosian | |
| 6,270,513 B1 | 8/2001 | Tsugita et al. | |
| 6,273,901 B1 | 8/2001 | Whitcher et al. | |
| 6,277,138 B1 | 8/2001 | Levinson et al. | |

| | | | | | |
|---|---|---|---|---|---|
| 6,277,139 B1 * | 8/2001 | Levinson et al. ............ 606/200 | 6,537,294 B1 | 3/2003 | Boyle et al. |
| 6,280,451 B1 | 8/2001 | Bates et al. | 6,537,295 B1 | 3/2003 | Peterson |
| 6,287,321 B1 | 9/2001 | Jang | 6,537,296 B2 | 3/2003 | Levinson et al. |
| 6,290,656 B1 | 9/2001 | Boyle et al. | 6,537,297 B2 | 3/2003 | Tsugita et al. |
| 6,290,710 B1 | 9/2001 | Cryer et al. | 6,540,722 B1 * | 4/2003 | Boyle et al. ................ 604/106 |
| 6,295,989 B1 | 10/2001 | Connors, III | 6,540,767 B1 | 4/2003 | Walak et al. |
| 6,306,163 B1 | 10/2001 | Fitz | 6,540,768 B1 | 4/2003 | Diaz et al. |
| 6,319,242 B1 | 11/2001 | Patterson et al. | 6,544,276 B1 | 4/2003 | Azizi |
| 6,319,268 B1 | 11/2001 | Ambrisco et al. | 6,544,279 B1 | 4/2003 | Hopkins et al. |
| 6,325,815 B1 | 12/2001 | Kusleika et al. | 6,544,280 B1 | 4/2003 | Daniel et al. |
| 6,336,934 B1 | 1/2002 | Gilson et al. | 6,547,759 B1 | 4/2003 | Fisher |
| 6,340,364 B2 | 1/2002 | Kanesaka | 6,551,268 B1 | 4/2003 | Kaganov et al. |
| 6,340,465 B1 | 1/2002 | Hsu et al. | 6,551,341 B2 | 4/2003 | Boylan et al. |
| 6,346,116 B1 | 2/2002 | Brooks et al. | 6,551,342 B1 | 4/2003 | Shen et al. |
| 6,348,056 B1 | 2/2002 | Bates et al. | 6,558,401 B1 | 5/2003 | Azizi |
| 6,355,051 B1 | 3/2002 | Sisskind et al. | 6,558,405 B1 | 5/2003 | McInnes |
| 6,361,545 B1 | 3/2002 | Macoviak et al. | 6,562,058 B2 | 5/2003 | Seguin |
| 6,361,546 B1 | 3/2002 | Khosravi | 6,565,591 B2 | 5/2003 | Kelly et al. |
| 6,364,895 B1 | 4/2002 | Greenhalgh | 6,569,184 B2 | 5/2003 | Huter |
| 6,364,896 B1 | 4/2002 | Addis | 6,575,995 B1 | 6/2003 | Huter et al. |
| 6,371,969 B1 | 4/2002 | Tsugita et al. | 6,575,996 B1 * | 6/2003 | Denison et al. ............. 606/200 |
| 6,371,970 B1 | 4/2002 | Khosravi et al. | 6,575,997 B1 | 6/2003 | Palmer et al. |
| 6,371,971 B1 | 4/2002 | Tsugita et al. | 6,582,447 B1 | 6/2003 | Patel et al. |
| 6,375,670 B1 | 4/2002 | Greenhalgh | 6,582,448 B1 | 6/2003 | Boyle et al. |
| 6,383,206 B1 | 5/2002 | Gillick et al. | 6,585,756 B1 | 7/2003 | Strecker |
| 6,384,062 B1 | 5/2002 | Ikeda et al. | 6,589,263 B1 | 7/2003 | Hopkins et al. |
| 6,391,044 B1 | 5/2002 | Yadav et al. | 6,589,265 B1 | 7/2003 | Palmer et al. |
| 6,394,978 B1 | 5/2002 | Boyle et al. | 6,592,546 B1 | 7/2003 | Barbut et al. |
| 6,395,014 B1 | 5/2002 | Macoviak et al. | 6,592,606 B2 | 7/2003 | Huter et al. |
| 6,398,756 B2 | 6/2002 | Peterson et al. | 6,592,607 B1 | 7/2003 | Palmer et al. |
| 6,402,771 B1 | 6/2002 | Palmer et al. | 6,592,616 B1 | 7/2003 | Stack et al. |
| 6,406,471 B1 | 6/2002 | Jang et al. | 6,596,011 B2 | 7/2003 | Johnson et al. |
| 6,423,032 B2 | 7/2002 | Parodi | 6,599,307 B1 | 7/2003 | Huter et al. |
| 6,423,086 B1 | 7/2002 | Barbut et al. | 6,599,308 B2 | 7/2003 | Amplatz |
| 6,425,909 B1 | 7/2002 | Dieck et al. | 6,602,269 B2 | 8/2003 | Wallace et al. |
| 6,428,559 B1 | 8/2002 | Johnson | 6,602,271 B2 | 8/2003 | Adams et al. |
| 6,432,122 B1 | 8/2002 | Gilson et al. | 6,602,272 B2 | 8/2003 | Boylan et al. |
| 6,436,121 B1 | 8/2002 | Blom | 6,602,273 B2 | 8/2003 | Marshall |
| 6,443,926 B1 | 9/2002 | Kletschka | 6,605,102 B1 | 8/2003 | Mazzocchi et al. |
| 6,443,971 B1 | 9/2002 | Boylan et al. | 6,605,111 B2 | 8/2003 | Bose et al. |
| 6,443,972 B1 | 9/2002 | Bosma | 6,607,506 B2 | 8/2003 | Kletschka |
| 6,443,979 B1 | 9/2002 | Stalker et al. | 6,610,077 B1 | 8/2003 | Hancock et al. |
| 6,447,530 B1 | 9/2002 | Ostrovsky et al. | 6,616,679 B1 | 9/2003 | Khosravi et al. |
| 6,447,531 B1 | 9/2002 | Amplatz | 6,616,680 B1 | 9/2003 | Thielen |
| 6,450,989 B2 | 9/2002 | Dubrul et al. | 6,616,681 B2 | 9/2003 | Hanson et al. |
| 6,458,139 B1 | 10/2002 | Palmer et al. | 6,616,682 B2 | 9/2003 | Joergensen et al. |
| 6,461,370 B1 | 10/2002 | Gray et al. | 6,620,148 B1 | 9/2003 | Tsugita et al. |
| 6,468,291 B2 | 10/2002 | Bates et al. | 6,620,182 B1 | 9/2003 | Khosravi |
| 6,482,222 B1 | 11/2002 | Bruckheimer et al. | 6,623,450 B1 | 9/2003 | Dutta |
| 6,485,456 B1 | 11/2002 | Kletschka | 6,629,953 B1 | 10/2003 | Boyd |
| 6,485,497 B2 | 11/2002 | Wensel et al. | 6,632,236 B2 | 10/2003 | Hogendijk |
| 6,485,500 B1 | 11/2002 | Kokish et al. | 6,632,241 B1 | 10/2003 | Hancock et al. |
| 6,485,501 B1 | 11/2002 | Green | 6,635,068 B1 | 10/2003 | Dubrul et al. |
| 6,485,502 B2 | 11/2002 | Don Michael et al. | 6,635,070 B2 | 10/2003 | Leeflang et al. |
| 6,485,507 B1 | 11/2002 | Walak et al. | 6,638,293 B1 | 10/2003 | Makowner et al. |
| 6,494,895 B2 | 12/2002 | Addis | 6,638,294 B1 | 10/2003 | Palmer |
| 6,499,487 B1 | 12/2002 | McKenzie et al. | 6,645,220 B1 | 11/2003 | Huter et al. |
| 6,500,166 B1 | 12/2002 | Zadno Azizi et al. | 6,645,221 B1 | 11/2003 | Richter |
| 6,506,203 B1 | 1/2003 | Boyle et al. | 6,645,223 B2 | 11/2003 | Boyle et al. |
| 6,506,205 B2 | 1/2003 | Goldberg et al. | 6,645,224 B2 | 11/2003 | Gilson et al. |
| 6,511,492 B1 | 1/2003 | Rosenbluth | 6,652,480 B1 | 11/2003 | Imran et al. |
| 6,511,496 B1 | 1/2003 | Huter et al. | 6,652,505 B1 | 11/2003 | Tsugita et al. |
| 6,511,497 B1 | 1/2003 | Braun et al. | 6,652,554 B1 | 11/2003 | Wholey et al. |
| 6,511,503 B1 | 1/2003 | Burkett et al. | 6,652,557 B1 | 11/2003 | MacDonald |
| 6,514,273 B1 | 2/2003 | Voss et al. | 6,656,202 B2 | 12/2003 | Papp et al. |
| 6,517,550 B1 | 2/2003 | Konya et al. | 6,656,203 B2 | 12/2003 | Roth et al. |
| 6,517,559 B1 | 2/2003 | O'Connell | 6,656,204 B2 | 12/2003 | Ambrisco et al. |
| 6,520,978 B1 | 2/2003 | Blackledge et al. | 6,656,351 B2 | 12/2003 | Boyle |
| 6,527,746 B1 | 3/2003 | Oslund et al. | 6,660,021 B1 | 12/2003 | Palmer et al. |
| 6,527,791 B2 | 3/2003 | Fisher | 6,663,650 B2 | 12/2003 | Sepetka et al. |
| 6,530,939 B1 | 3/2003 | Hopkins et al. | 6,663,651 B2 | 12/2003 | Krolik et al. |
| 6,530,940 B2 | 3/2003 | Fisher | 6,663,652 B2 | 12/2003 | Daniel et al. |
| 6,533,800 B1 | 3/2003 | Barbut | 6,673,090 B2 | 1/2004 | Root et al. |

| Patent | Date | Inventor |
|---|---|---|
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B2 | 8/2006 | Broome et al. |
| 7,097,651 B2 | 8/2006 | Harrison et al. |
| 7,097,834 B1 | 8/2006 | Boyle et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2001/0012951 A1 | 8/2001 | Bates et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |

| | | | | | | |
|---|---|---|---|---|---|---|
| 2002/0128681 A1 | 9/2002 | Broome et al. | | 2003/0150821 A1 | 8/2003 | Bates et al. |
| 2002/0133092 A1 | 9/2002 | Oslund et al. | | 2003/0153935 A1 | 8/2003 | Mialhe |
| 2002/0138094 A1 | 9/2002 | Borillo et al. | | 2003/0153942 A1 | 8/2003 | Wang et al. |
| 2002/0138095 A1 | 9/2002 | Mazzocchi et al. | | 2003/0153943 A1 | 8/2003 | Michael et al. |
| 2002/0143360 A1 | 10/2002 | Douk et al. | | 2003/0158574 A1 | 8/2003 | Esch et al. |
| 2002/0143361 A1 | 10/2002 | Douk et al. | | 2003/0163064 A1 | 8/2003 | Kusleika et al. |
| 2002/0151927 A1 | 10/2002 | Douk et al. | | 2003/0171770 A1 | 9/2003 | Anderson et al. |
| 2002/0156456 A1 | 10/2002 | Fisher | | 2003/0171771 A1 | 9/2003 | Shimon |
| 2002/0156457 A1 | 10/2002 | Fisher | | 2003/0171803 A1 | 9/2003 | Berrada et al. |
| 2002/0161390 A1 | 10/2002 | Mouw | | 2003/0176884 A1 | 9/2003 | Broome et al. |
| 2002/0161392 A1 | 10/2002 | Dubrul | | 2003/0176885 A1 | 9/2003 | Wholey et al. |
| 2002/0161393 A1 | 10/2002 | Demond et al. | | 2003/0176886 A1 | 9/2003 | Sutton et al. |
| 2002/0161395 A1 | 10/2002 | Douk et al. | | 2003/0176889 A1 | 9/2003 | Boyle et al. |
| 2002/0165576 A1 | 11/2002 | Boyle et al. | | 2003/0181942 A1 | 9/2003 | Sutton et al. |
| 2002/0169414 A1 | 11/2002 | Kletschka | | 2003/0181943 A1 | 9/2003 | Daniel et al. |
| 2002/0169458 A1 | 11/2002 | Connors, III | | 2003/0187474 A1 | 10/2003 | Keegan et al. |
| 2002/0169472 A1 | 11/2002 | Douk et al. | | 2003/0187475 A1 | 10/2003 | Tsugita et al. |
| 2002/0169474 A1 | 11/2002 | Kusleika et al. | | 2003/0187495 A1 | 10/2003 | Cully et al. |
| 2002/0173815 A1 | 11/2002 | Hogendijk et al. | | 2003/0191493 A1 | 10/2003 | Epstein et al. |
| 2002/0173817 A1 | 11/2002 | Kletschka et al. | | 2003/0195554 A1 | 10/2003 | Shen et al. |
| 2002/0188313 A1 | 12/2002 | Johnson et al. | | 2003/0195555 A1 | 10/2003 | Khairkhahan et al. |
| 2002/0188314 A1 | 12/2002 | Anderson et al. | | 2003/0195556 A1 | 10/2003 | Stack et al. |
| 2002/0193825 A1 | 12/2002 | McGuckin et al. | | 2003/0199819 A1 | 10/2003 | Beck |
| 2002/0193826 A1 | 12/2002 | McGuckin et al. | | 2003/0199921 A1 | 10/2003 | Palmer et al. |
| 2002/0193827 A1 | 12/2002 | McGuckin et al. | | 2003/0204168 A1 | 10/2003 | Bosme et al. |
| 2002/0193828 A1 | 12/2002 | Griffin et al. | | 2003/0204202 A1 | 10/2003 | Palmer et al. |
| 2003/0004536 A1 | 1/2003 | Boylan et al. | | 2003/0208222 A1 | 11/2003 | Zadno-Azizi |
| 2003/0004537 A1 | 1/2003 | Boyle et al. | | 2003/0208224 A1 | 11/2003 | Broome |
| 2003/0004539 A1 | 1/2003 | Linder et al. | | 2003/0208225 A1 | 11/2003 | Goll et al. |
| 2003/0004540 A1 | 1/2003 | Linder et al. | | 2003/0208226 A1 | 11/2003 | Bruckheimer et al. |
| 2003/0004541 A1 | 1/2003 | Linder et al. | | 2003/0208227 A1 | 11/2003 | Thomas |
| 2003/0009188 A1 | 1/2003 | Linder et al. | | 2003/0208228 A1 | 11/2003 | Gilson et al. |
| 2003/0009189 A1 | 1/2003 | Gilson et al. | | 2003/0208229 A1 | 11/2003 | Kletschka |
| 2003/0015206 A1 | 1/2003 | Roth et al. | | 2003/0212361 A1 | 11/2003 | Boyle et al. |
| 2003/0018354 A1 | 1/2003 | Roth et al. | | 2003/0212429 A1 | 11/2003 | Keegan et al. |
| 2003/0023265 A1 | 1/2003 | Forber | | 2003/0212431 A1 | 11/2003 | Brady et al. |
| 2003/0028238 A1 | 2/2003 | Burkett et al. | | 2003/0212434 A1 | 11/2003 | Thielen |
| 2003/0032941 A1 | 2/2003 | Boyle et al. | | 2003/0216774 A1 | 11/2003 | Larson |
| 2003/0032977 A1 | 2/2003 | Brady et al. | | 2003/0220665 A1 | 11/2003 | Eskuri et al. |
| 2003/0040772 A1 | 2/2003 | Hyodoh et al. | | 2003/0225418 A1 | 12/2003 | Eskuri et al. |
| 2003/0042186 A1 | 3/2003 | Boyle et al. | | 2003/0225435 A1 | 12/2003 | Huter et al. |
| 2003/0045898 A1 | 3/2003 | Harrison et al. | | 2003/0229295 A1 | 12/2003 | Houde et al. |
| 2003/0057156 A1 | 3/2003 | Peterson et al. | | 2003/0229374 A1 | 12/2003 | Brady et al. |
| 2003/0060782 A1 | 3/2003 | Bose et al. | | 2003/0233117 A1 | 12/2003 | Adams et al. |
| 2003/0060843 A1 | 3/2003 | Boucher | | 2003/0236545 A1 | 12/2003 | Gilson |
| 2003/0060844 A1 | 3/2003 | Borillo et al. | | 2004/0002730 A1 | 1/2004 | Denison et al. |
| 2003/0065354 A1 | 4/2003 | Boyle et al. | | 2004/0006361 A1 | 1/2004 | Boyle et al. |
| 2003/0069596 A1 | 4/2003 | Eskuri | | 2004/0006364 A1 | 1/2004 | Ladd |
| 2003/0069597 A1 | 4/2003 | Petersen | | 2004/0006365 A1 | 1/2004 | Brady et al. |
| 2003/0078519 A1 | 4/2003 | Salahieh et al. | | 2004/0006366 A1 | 1/2004 | Huter et al. |
| 2003/0078614 A1 | 4/2003 | Satahieh et al. | | 2004/0006367 A1 | 1/2004 | Johnson et al. |
| 2003/0083692 A1 | 5/2003 | Vrba et al. | | 2004/0006368 A1 | 1/2004 | Mazzocchi et al. |
| 2003/0083693 A1 | 5/2003 | Daniel et al. | | 2004/0015184 A1 | 1/2004 | Boyle et al. |
| 2003/0100917 A1 | 5/2003 | Boyle et al. | | 2004/0019363 A1 | 1/2004 | Hanson et al. |
| 2003/0100918 A1 | 5/2003 | Duane | | 2004/0034385 A1 | 2/2004 | Gilson et al. |
| 2003/0105484 A1 | 6/2003 | Boyle et al. | | 2004/0039411 A1 | 2/2004 | Gilson et al. |
| 2003/0109824 A1 | 6/2003 | Anderson et al. | | 2004/0044359 A1 | 3/2004 | Renati et al. |
| 2003/0114879 A1 | 6/2003 | Euteneuer et al. | | 2004/0044360 A1 | 3/2004 | Lowe |
| 2003/0114880 A1 | 6/2003 | Hansen et al. | | 2004/0049226 A1 | 3/2004 | Keegan et al . |
| 2003/0120303 A1 | 6/2003 | Boyle et al. | | 2004/0059372 A1 | 3/2004 | Tsugita |
| 2003/0130680 A1 | 7/2003 | Russell | | 2004/0059373 A1 | 3/2004 | Shapiro et al. |
| 2003/0130681 A1 | 7/2003 | Ungs | | 2004/0082697 A1 | 4/2004 | Broome et al. |
| 2003/0130682 A1 | 7/2003 | Broome et al. | | 2004/0082968 A1 | 4/2004 | Krolik et al. |
| 2003/0130684 A1 | 7/2003 | Brady et al. | | 2004/0088000 A1 | 5/2004 | Muller |
| 2003/0130685 A1 | 7/2003 | Daniel et al. | | 2004/0088002 A1 | 5/2004 | Boyle et al. |
| 2003/0130686 A1 | 7/2003 | Daniel et al. | | 2004/0093009 A1 | 5/2004 | Denison et al. |
| 2003/0130687 A1 | 7/2003 | Daniel et al. | | 2004/0093010 A1 | 5/2004 | Gesswein et al. |
| 2003/0130688 A1 | 7/2003 | Daniel et al. | | 2004/0093011 A1 | 5/2004 | Vrba |
| 2003/0135162 A1 | 7/2003 | Deyette, Jr. et al. | | 2004/0093012 A1 | 5/2004 | Cully et al. |
| 2003/0135232 A1 | 7/2003 | Douk et al. | | 2004/0093013 A1 | 5/2004 | Brady et al. |
| 2003/0139764 A1 | 7/2003 | Levinson et al. | | 2004/0098022 A1 | 5/2004 | Barone |
| 2003/0144685 A1 | 7/2003 | Boyle et al. | | 2004/0098026 A1 | 5/2004 | Joergensen et al. |
| 2003/0144689 A1 | 7/2003 | Brady et al. | | 2004/0098032 A1 | 5/2004 | Papp et al. |

| | | |
|---|---|---|
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salaheih et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boylan et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGucklin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |

| | | | |
|---|---|---|---|
| 2006/0184194 A1 | 8/2006 | Pal et al. | |
| 2006/0190025 A1 | 8/2006 | Lehe et al. | |
| 2006/0195137 A1 | 8/2006 | Sepetka et al. | |
| 2006/0195138 A1 | 8/2006 | Goll et al. | |
| 2006/0200047 A1 | 9/2006 | Galdonik et al. | |
| 2006/0200191 A1 | 9/2006 | Zadno-Azizi | |
| 2006/0206139 A1 | 9/2006 | Tekulve | |

FOREIGN PATENT DOCUMENTS

| | | |
|---|---|---|
| EP | 0 472 334 A1 | 2/1992 |
| EP | 0533511 A1 | 3/1993 |
| EP | 1 127 556 A2 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO 99/16382 | 4/1999 |
| WO | WO 99/22673 | 5/1999 |
| WO | WO99/23976 | 5/1999 |
| WO | WO99/44510 | 9/1999 |
| WO | WO 99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |

* cited by examiner

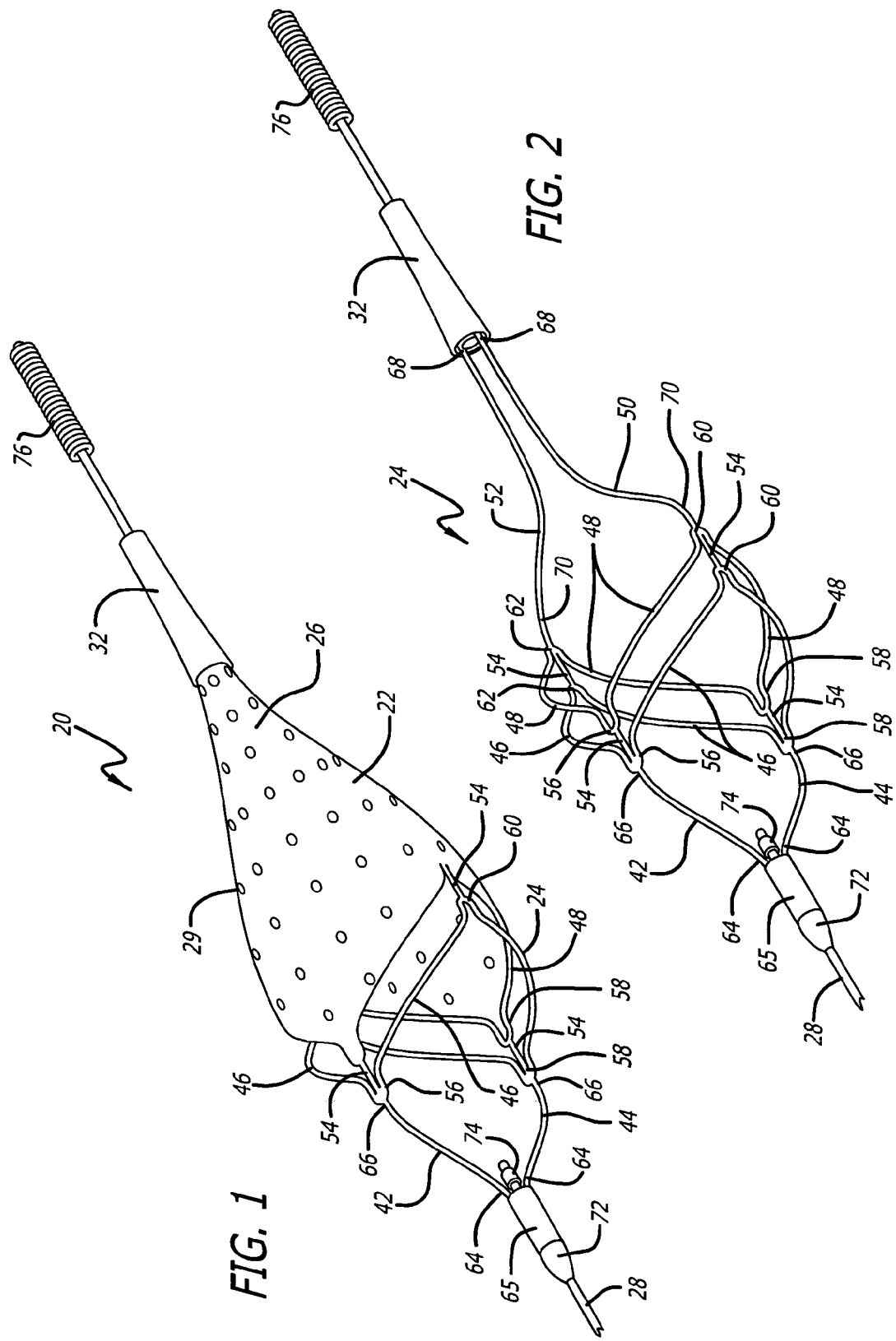

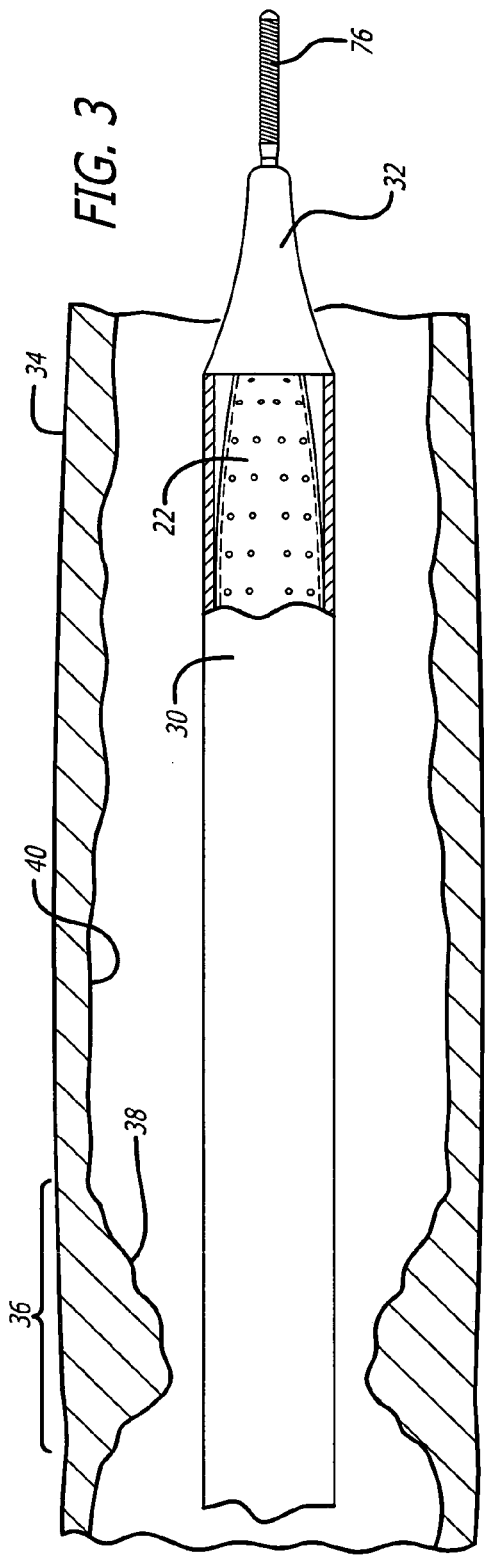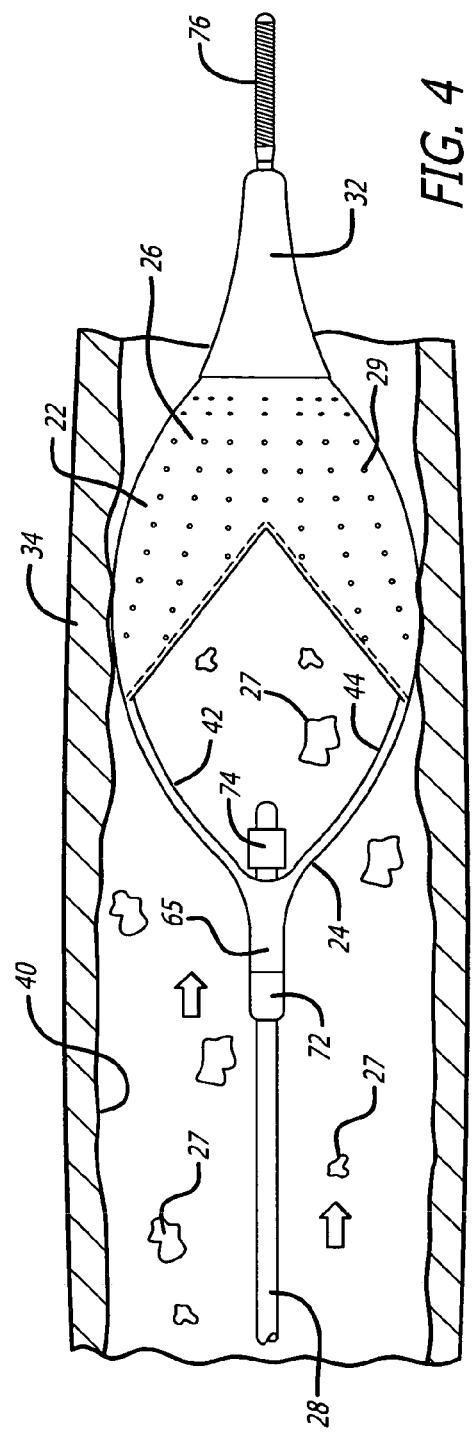

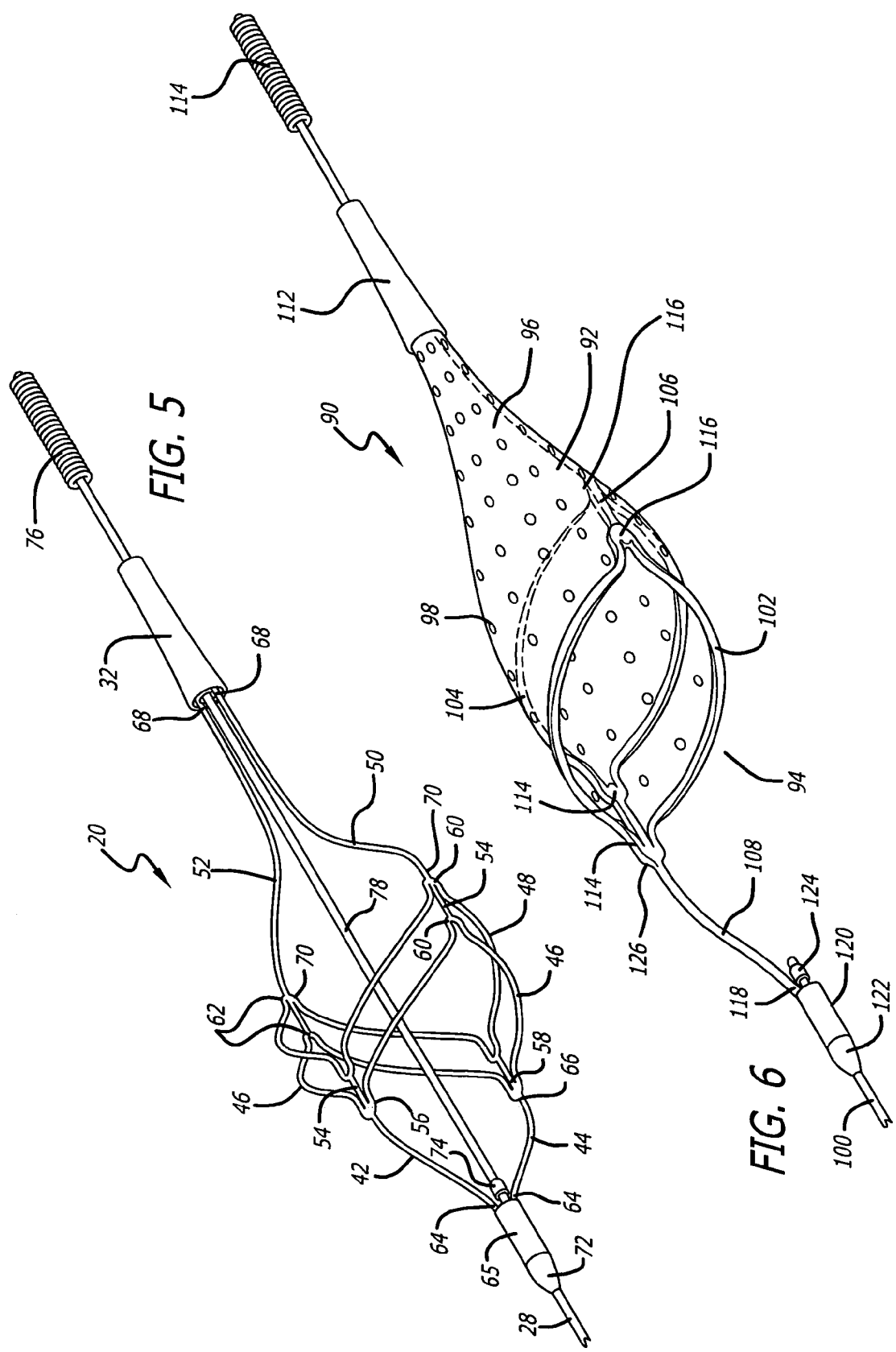

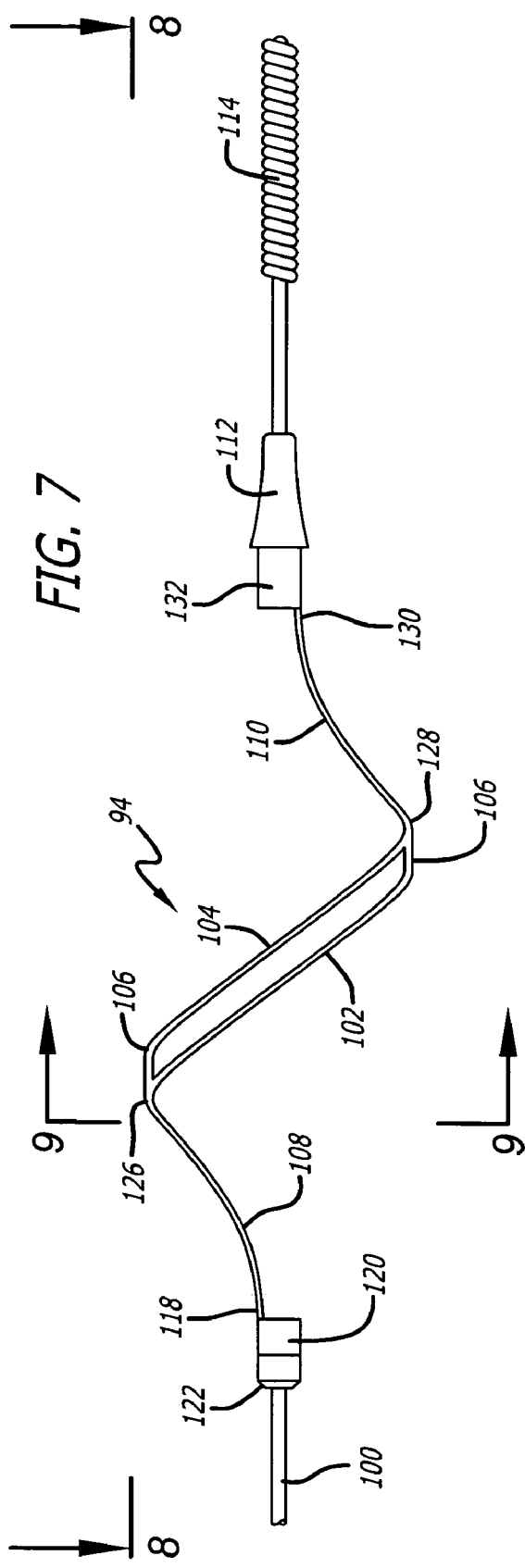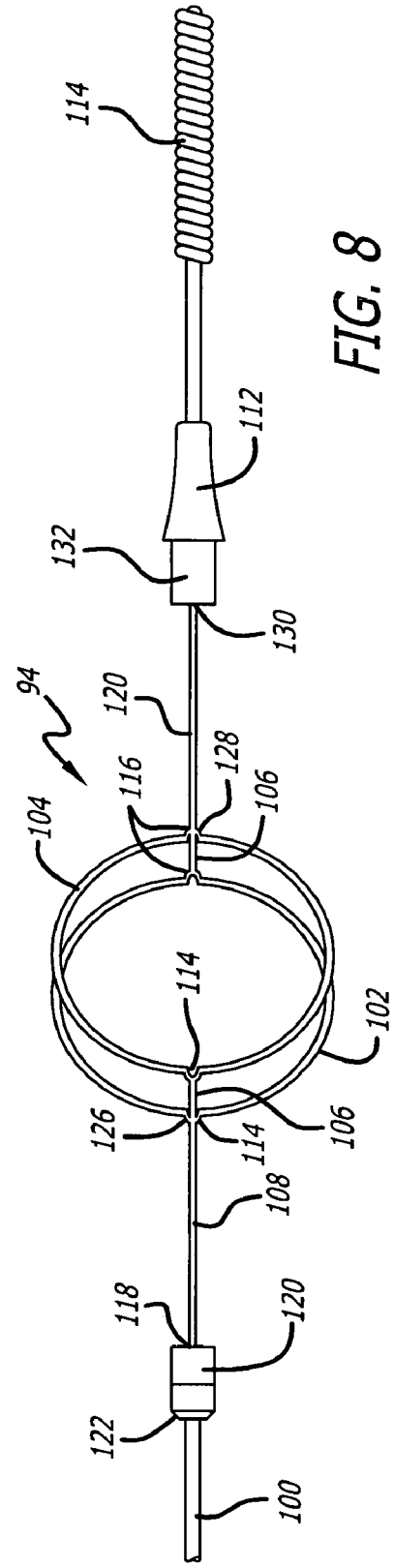
FIG. 7
FIG. 8

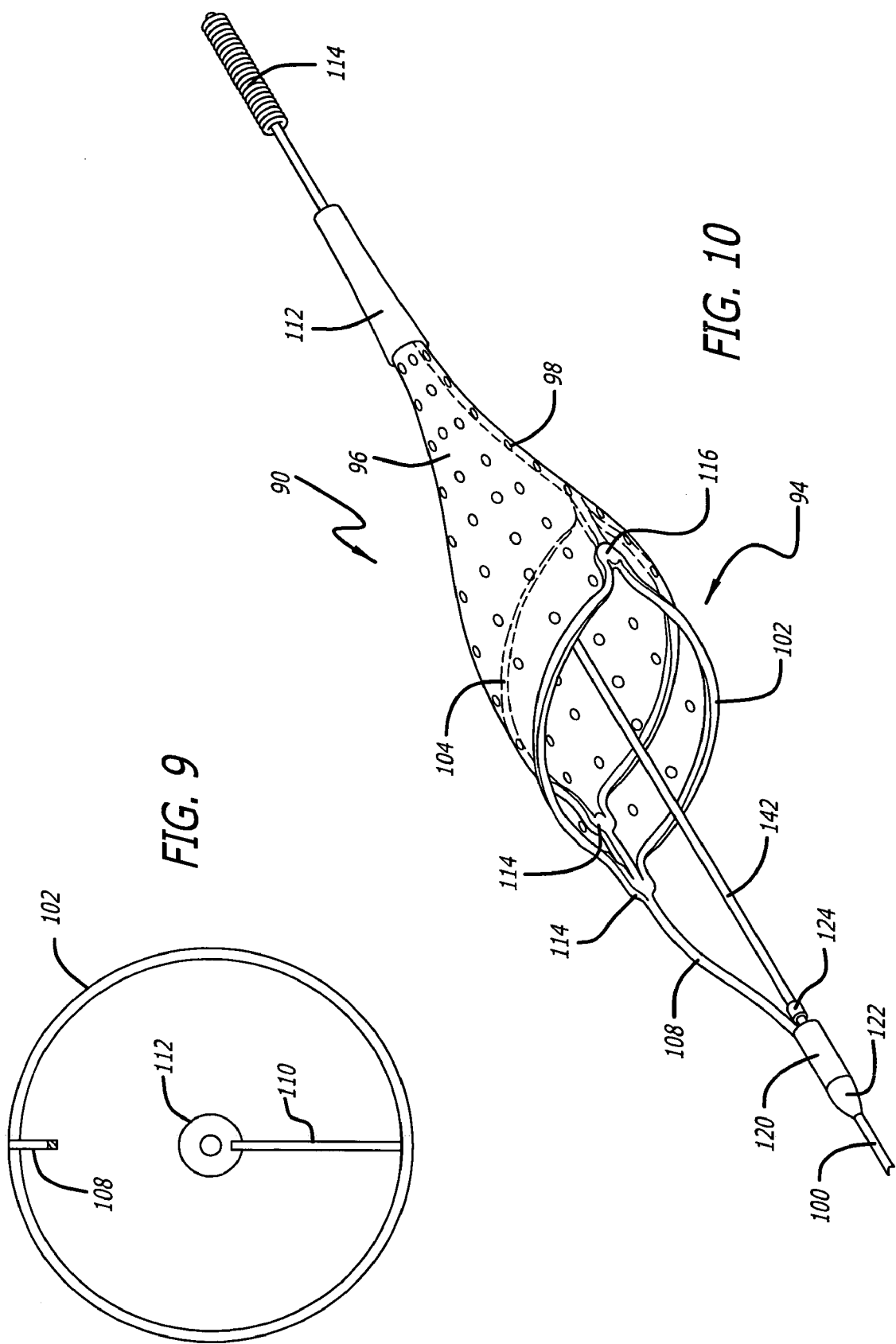

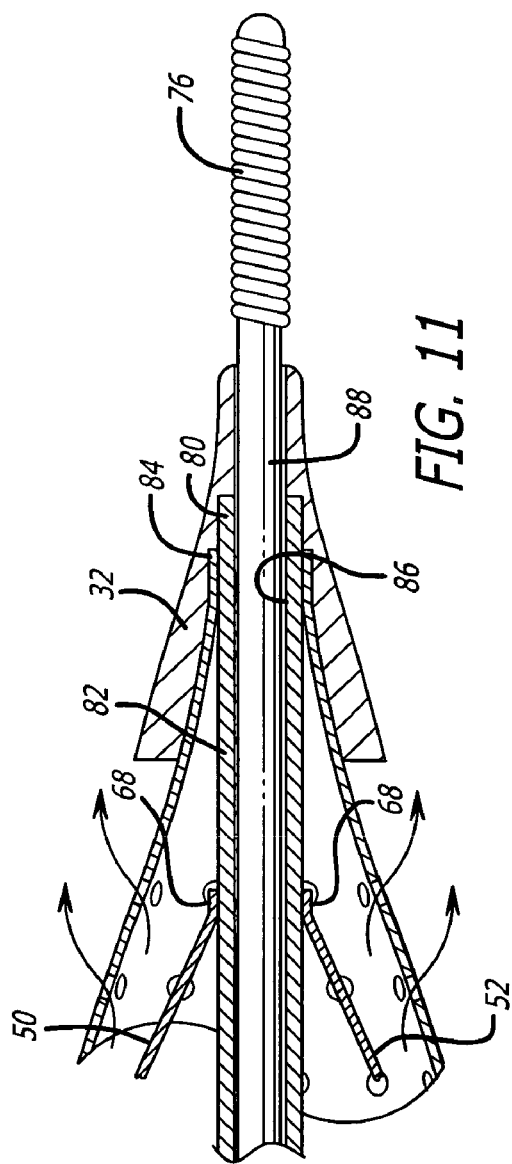
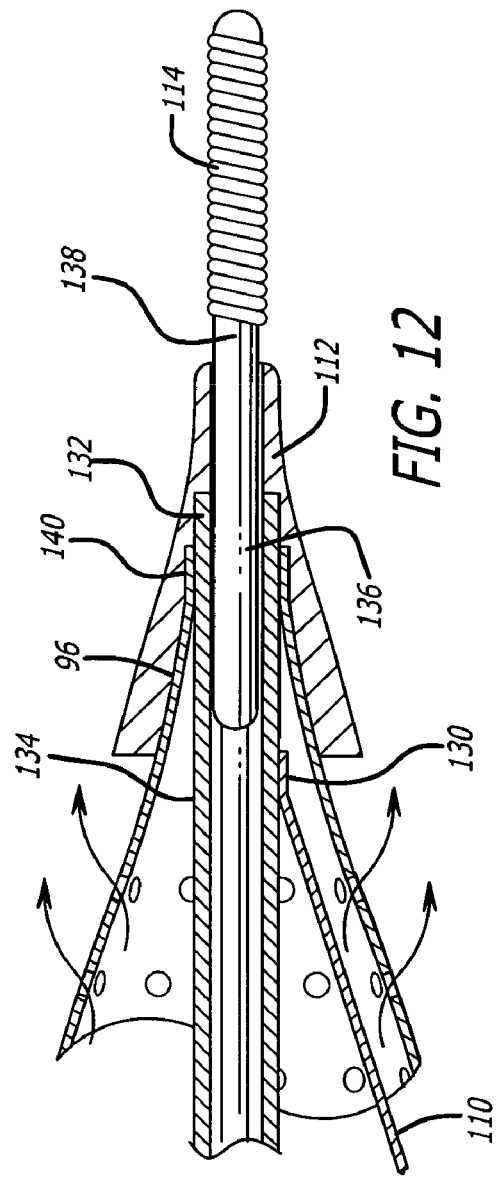

FLEXIBLE AND CONFORMABLE EMBOLIC FILTERING DEVICES

FIELD OF THE INVENTION

The present invention relates generally to filtering devices used when an interventional procedure is being performed in a stenosed or occluded region of a body vessel to capture embolic material that may be created and released into the vessel during the procedure. The present invention is more particularly directed to an embolic filtering device made with an expandable cage possessing good flexibility and bendability, which allows the embolic filtering device to be readily deployed in a bend in a body lumen of a patient.

BACKGROUND OF THE INVENTION

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occuring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters vessel are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Expandable filters can be provided with some increased flexibility by forming the struts of the filter assembly from relatively thin material. However, the use of thin material often can reduce the radiopacity of the expandable filter, often making it difficult for the physician to see the filter under fluoroscopy during deployment. Conversely, the use of thicker materials, which can promote radiopacity of the expandable filter, usually reduces its flexibility, which may impair the deliverability of the expandable filter within the patient.

What has been needed is an expandable filter assembly having high flexibility and bendability with sufficient strength and radiopacity to be successfully deployed within a patient's vasculature to collect embolic debris which may be released into the patient's vasculature.

SUMMARY OF THE INVENTION

The present invention provides a highly flexible cage (also referred to as a "basket") for use with an embolic filtering device designed to capture embolic debris created during the performance of a therapeutic interventional procedure, such as a balloon angioplasty or stenting procedure, in a body vessel. The present invention provides the physician with an embolic filtering device having high flexibility to be steered through tortuous anatomy, but yet possessing sufficient strength to hold open a filtering element against the wall of the body vessel for capturing embolic debris. An embolic filtering device made in accordance with the present invention is relatively easy to deploy, has good visibility under fluoroscopy, and has good flexibility and is conformable to the patient's anatomy.

An expandable cage made in accordance with the present invention from a self-expanding material, for example, nickel titanium (NiTi) or spring steel, and includes a number of outwardly extending struts capable of expanding from a collapsed position having a first delivery diameter to an expanded or deployed position having a second implanted diameter. A filter element made from an embolic-capturing material is attached to the expandable cage to move between a collapsed position and a deployed position.

The struts of the cage can be set to remain in the expanded, deployed position until an external force is placed over the struts to collapse and move the struts to the collapsed position. One way of accomplishing this is through the use of a restraining sheath, for example, which can be placed over the filtering device in a coaxial fashion to contact the cage and move the cage into the collapsed position. The embolic filtering device can be placed in the patient's vasculature and remain there for a period of time. The filtering device can be attached to the distal end of an elongated member, such as a guide wire, for temporary placement in the vasculature to capture emboli created during an interventional procedure. A guide wire may be used in conjunction with the filtering device when embolic debris is to be filtered during an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the basket into the expanded position. This can be easily performed by the physician by simply retracting the proximal end of the restraining sheath (located outside of the patient). Once the restraining sheath is retracted, the self-expanding properties of the cage cause each strut to move in a outward, radial fashion away from the guide wire to contact the wall of the body vessel. As the struts expand radially, so does the filter element which will now be maintained in place to collect embolic debris that may be released into the bloodstream as the physician performs the interventional procedure. The guide wire can then be used by the physician to deliver the necessary interventional device into the area of treatment. The deployed filter element captures embolic debris created and released into the body vessel during the interventional procedure.

In one aspect of the present invention, the enhanced flexibility and bendability of the embolic filtering device is achieved through the utilization of a unique cage design having a highly flexible and conformable circumferential member which is adapted to expand and conform to the size and shape of the body vessel. The expandable cage further includes at least one proximal strut having an end connected to a guide wire and the other end attached to the circumferential member. At least one distal strut is attached to the circumferential member and has its other end attached to the guide wire. The filter element is attached to the circumferential member and will open and close as the expandable cage moves between its expanded, deployed position and its unexpanded, delivery position. The circumferential member is self-expanding and is made from a highly flexible material which allows it to conform to the particular size and shape of the body vessel. This high flexibility and conformability of the circumferential member allows it to deployed in curved sections of the patient's anatomy and other eccentric vessel locations having non-circular shaped lumens. This allows an embolic filtering device made in accordance with the present invention to be deployed in locations in the patient's anatomy which might not be otherwise suitable for stiffer filtering devices. Moreover, due to the high flexibility and conformability of the circumferential member, an embolic filtering device made in accordance with present invention is less likely to create gaps between the filtering element and the wall of the vessel once deployed in the lumen. Therefore, the potential release of embolic debris past the deployed filter can be reduced.

In another aspect of the present invention, bending regions formed on the circumferential member help to actuate the circumferential member between its unexpanded and expanded positions. In one aspect of the present invention, these bending regions are substantially U-shaped bends formed on the circumferential member at various locations along the member. While the circumferential member itself is self-expanding and capable of moving between these positions, the bending regions further enhance the actuation of the circumferential member between these positions. In one particular aspect of the present invention, the proximal strut is attached directly to this bending region. Likewise, a distal strut can be attached to a second bend section. In this fashion, a highly bendable and conformable cage can be produced which should conform to the particular shape of the body vessel once deployed.

In other aspects of the present invention, a pair of circumferential members can be utilized to create the expandable cage which maintains a high degree of bendability and conformability, but yet is sufficiently rigid enough to maintain the filtering element in an expanded position once the filtering device is fully deployed. Still other aspects of the present invention utilize a pair of proximal struts and a pair of distal struts to form a larger expandable cage which still retains good bendability and conformability, yet possesses sufficiently radial strength when deployed to maintain proper wall apposition between the filter element and the body vessel.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1 is a perspective view of an embolic filtering device embodying features of the present invention.

FIG. 2 is a perspective view of the expandable cage which forms part of the embolic filtering device of FIG. 1.

FIG. 3 is an elevational view, partially in cross section, of an embolic filtering device embodying features of the present invention as it is being delivered within a body vessel downstream from an area to be treated.

FIG. 4 is an elevational view, partially in cross section, similar to that shown in FIG. 3, wherein the embolic filtering device is deployed in its expanded position within the body vessel.

FIG. 5 is a perspective view of an alternative embodiment of an expandable cage similar to the cage of FIG. 2 which is attached to a guide wire that extends through the expandable cage to the distal end of the cage.

FIG. 6 is another particular embodiment of an embolic filtering device embodying features of the present invention.

FIG. 7 is an side elevational view of the expandable cage which forms part of the embolic filtering device shown in FIG. 6.

FIG. 8 is a top plan view of the expandable cage of FIG. 7 taken along line 8—8.

FIG. 9 is an end view of the expandable cage of FIG. 7 taken along line 9—9.

FIG. 10 is an alternative embodiment of an embolic filtering device embodying features of the present invention which utilizes a similar expandable cage as shown in FIG. 5.

FIG. 11 is an elevational view, partially in cross-section, of the distal end of the embolic filtering device of FIG. 1.

FIG. 12 is an elevational view, partially in cross-section, of the distal end of the embolic filtering device of FIG. 10.

DETAILED DESCRIPTION OF THE PREFERRED EMBODIMENTS

Turning now to the drawings, in which like reference numerals represent like or corresponding elements in the drawings, FIGS. 1 and 2 illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding basket or cage 24 and a filter element 26 attached thereto. In this particular embodiment, the expandable filter assembly 22 is rotatably mounted on the distal end of an elongated (solid or hollow) cylindrical tubular shaft, such as a guide wire 28. The guide wire has a proximal end (not shown) which extends outside the patient and is manipulated by the physician to deliver the filter assembly into the target area in the patient's vasculature. A restraining or delivery sheath 30 (FIG. 3) extends coaxially along the guide wire 28 in order to maintain the expandable filter assembly 22 in its collapsed position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding cage 24 immediately begins to expand within the body vessel (see FIG. 4), causing the filter element 26 to expand as well.

An obturator 32 affixed to the distal end of the filter assembly 32 can be implemented to prevent possible "snowplowing" of the embolic filtering device as it is being delivered through the vasculature. The obturator can be made from a soft polymeric material, such as Pebax 40D, and has a smooth surface to help the embolic filtering device travel through the vasculature and cross lesions while preventing the distal end of the restraining sheath 30 from "digging" or "snowplowing" into the wall of the body vessel.

In FIGS. 3 and 4, the embolic filtering device 20 is shown as it is being delivered within an artery 34 or other body vessel of the patient. Since the embolic filtering device made in accordance with the present invention possesses excellent bendability and flexibility, it will conform well to the shape of the vasculature while allowing the filter assembly to more easily negotiate a curved radius in the patient's vasculature.

Referring now to FIG. 4, the embolic filtering device 22 is shown in its expanded position within the patient's artery 34. This portion of the artery 34 has an area of treatment 36 in which atherosclerotic plaque 38 has built up against the inside wall 40 of the artery 34. The filter assembly 22 is to be placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The cage 24 includes self-expanding struts which, upon release from the restraining sheath 30, expand the filter element 26 into its deployed position within the artery (FIG. 4). Embolic particles 27 created during the interventional procedure and released into the bloodstream are captured within the deployed filter element 26. The filter may include perfusion openings 29, or other suitable perfusion means, for allowing blood flow through the filter 26. The filter element will capture embolic particles which are larger than the perfusion openings while allowing some blood to perfuse downstream to vital organs. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) could be implanted in the area of treatment 36 using over-the-wire techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and should enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

Referring again to FIGS. 1 and 2, the expandable cage 24 includes a pair of self-expanding proximal struts 42 and 44 which help to deploy the filter element 26 and the remainder of the expandable cage. These proximal struts 42 and 44 are coupled to a first circumferential member 46 which is adapted to move from the unexpanded delivery position (FIG. 3) to the expanded deployed position (FIG. 4). A second circumferential member 48 is, in turn, coupled to the first circumferential member 46. The deployment of the first and second circumferential members 46 and 48 results in the filter element 26 being placed against the wall 40 of the artery or other body vessel, even if the lumen of the body vessel is non-circular. A pair of distal struts 50 and 52 connected to the second circumferential member 48 extend distally towards the obturator 32. The first and second circumferential members 46 and 48 are coupled to, and spaced apart, from each other by short connecting struts 54. It should be appreciated that a single circumferential member could be used to create an expandable cage made in accordance with the present invention. Also, additional circumferential members could be added to create a larger expandable cage. Additionally, while only two proximal struts and distal struts are shown in the cage design of FIGS. 1–5, the cage could also be made with a single proximal and distal strut (see FIGS. 6–10) or additional struts (not shown) could be implemented without departing from the spirit and scope of the present invention.

As can be seen in FIGS. 1 and 2, each circumferential member includes four bending regions 56, 58, 60 and 62 formed on the circumferential member to enhance the performance of the circumferential member to bend as it moves between the unexpanded and expanded positions. In the particular embodiment shown in FIG. 2, each bending region 56–62 is placed on the circumferential member approximately 90 degrees apart. In this regard, as can be seen in FIGS. 1 and 2, the bending regions 56, 58, 60 and 62 on the first circumferential member 46 align with the same bending regions 56, 58, 60 and 20 of the second circumferential member 48. This alignment of bending regions on the first and second circumferential members 46 and 48 is referred to as "in phase." In this regard, the proximal bending regions 56 and 58 of the first and second circumferential members 46 and 48 are attached to and aligned next to each other. The same is true for the distal bending regions 50 and 52. Each of the proximal struts includes a first end 64 attached to the collar 65 which is rotatably mounted to the guide wire 28. Each proximal strut includes a second end 66 connected to one of the proximal bending regions 56 and 58 of the first circumferential member 46. These proximal bending regions 56 and 58 are spaced approximately 180 degrees apart from each other along a circular diameter defined by the expanded circumferential member 46. Each of the distal struts 50 and 52, in turn, has a first end 68 connected to and extending towards the obturator 32 and a second end 70 attached to the distal bending regions 60 and 62 of the second circumferential member 48. These distal bending regions 60 and 62, in turn, are spaced approximately 180 degrees apart from each other and are offset 90 degrees from the proximal bending regions 56 and 58.

Each of the bending regions is substantially U-shaped which help to create a natural bending point on the circumferential member. While the flexibility of the circumferential members is already high, these bending regions only help to increase the ability of the circumferential member to collapse or expand when needed.

In this manner, the shape of the hinge regions creates a natural hinge that helps to actuate the expandable cage between the unexpanded and expanded positions. As can be best seen in FIG. 2, the U-shaped bending regions 54 and 56 are positioned directly opposite the U-shaped portion of the distal bending regions 58 and 60. The positioning of the direction of the U portion also enhances the ability of the circumferential member to bend. These circumferential members 46 and 48, while being quite bendable, nevertheless maintain sufficient radial strength to remain in the deployed position to hold the filter element 26 open in the body vessel for collecting embolic particles which may be entrained in the body fluid.

The shape of the bending regions are shown as substantially U-shaped portions, however, any one of a number of different shapes could also be utilized to create a natural bending point on the circumferential member. For example, a V-shaped region could also be formed and would function similarly to a U-shaped portion to facilitate the collapse and expansion of the circumferential member as needed. Alternative shapes and sizes of the bending regions also could be utilized without departing from the spirit and scope of the invention. Although four bending regions are shown on each circumferential member, it should be appreciated that the number of different bending regions could be increased or decreased as needed. For example, it is possible to utilize only two bending regions, as is shown in the embodiment of the expandable cage of FIG. 6, in order to facilitate bending. Additional bending regions also could be utilized in the event that additional proximal or distal struts are used to form the expandable cage. Moreover, different sizes, shapes and location of the bending regions can be utilized on any circumferential member.

The expandable cage 24 of FIGS. 1 and 2 is shown rotatably mounted to the distal end of the guide wire 28 to allow the entire filtering assembly 22 to remain stationary once deployed in the body vessel. This feature prevents the filtering assembly from rotating in the event that the proximal end of the guide wire is accidentally rotated by the physician during use. As a result, the possibility that the deployed filtering assembly 22 could be rotated to cause trauma to the wall of the vessel is minimized. Referring specifically to FIGS. 1 and 2, the first end 64 of the proximal struts 42 and 44 are attached to the collar 65 which is rotatably mounted on the guide wire 28 between a pair of stop fittings 72 and 74. The stop fittings 72 and 74 allow the expandable cage 24 to spin on the guide wire but restricts the longitudinal movement of the cage on the guide wire. This particular mechanism is but one way to rotatably mount the expandable cage 24 to the guide wire 28.

The expandable cage is shown in FIGS. 1 and 2 does not include a segment of guide wire which would otherwise extend through the expandable cage 24 to the distal end where the coil tip 76 extends through the obturator 32. In this manner, the elimination of this short segment of guide wire through the expandable cage 24 may help collapse the filter assembly 22 to a smaller delivery profile. The lack of the guide wire segment also may help to increase the flexibility and bendability of the filtering assembly 22 somewhat as it is being delivered through the patient's vasculature.

Referring now to FIG. 5, an alternative version of the embolic filtering device 20 is shown as it is rotatably mounted onto a guide wire 28. In FIG. 5, the filter element has been removed to better show the portion of the guide wire which extends through the expandable cage to the coil tip of the guide wire. In this particular embodiment, a short segment of guide wire 78 is present and extends through the expandable cage 24 and extends through the obturator 32. This particular embodiment of the embolic filtering device functions in the same fashion as the filter device shown and described in FIGS. 1–4. However, a fill-length guide wire is utilized in conjunction with this particular embodiment. While this particular embodiment of the filtering device may not be collapsed to a smaller profile as the one shown in FIGS. 1 and 2, nevertheless it has the advantage of a fill-length guide wire which allows the physician to manipulate the proximal end of the guide wire in order to steer the device in the patient's vasculature. The expandable cage 24 would be rotatably mounted on the guide wire as the proximal collar would be placed between two stop fittings located on the guide wire. One benefit from this particular embodiment stems from the ability of the physician to control the proximal end of the guide wire in order to steer the distal coil tip 76 into the desired vessel when delivering the device through the patient's vasculature. The embodiment of the filtering device shown in FIG. 1, while having its own advantages, does not allow the guide wire itself to be rotated at its proximal end of the guide wire to steer the distal coil tip 76 of the guide wire. However, the composite delivery sheath utilized to restrain and maintain the expandable filter in its collapsed position during delivery could be rotated by the physician to steer the coil tip into the desired vessel. In this manner, the proximal end of the delivery sheath could be torqued by the physician to rotate the distal coil wire into the target location. Alternatively, the particular design shown in FIG. 1 could also be modified so that the distal end of the guide wire, rather than being rotatably connected to the cage 24, is permanently attached together. In such a modification, the first ends of the proximal struts 42 and 44 could be simply bonded or otherwise fastened directly to the guide wire such that the expandable cage will rotate as the guide wire is being rotated. This particular embodiment would allow the physician to simply torque the proximal end of the guide wire to steer the distal coil into the desired area of treatment.

Referring now to FIG. 11, one manner in which the distal ends 68 of the distal struts 52 and 50 could be attached to the obturator 32 as shown. As can be seen in FIG. 11, the distal ends 68 are attached to a tubular member 80 which extends into the obturator 32. The ends 68 are attached to the outer surface 82 of the tubular member 80. The filter 26 tapers to a distal end 84 which is, in turn, bonded or otherwise adhesively attached to the outer surface 82 of this tubular member 80. Likewise, at least a portion of the tubular member 80 is in contact with the obturator 32 and is adhesively bonded or otherwise affixed thereto. The inner surface 86 of the tubular member 80 is in turn attached to a short segment 88 of the guide wire which extends out to the distal coil tip 76. In this manner, the short segment 88 of the guide wire is adhesively bonded or otherwise attached to the inner surface 68 to remain in place. The combination of elements thus form an integral distal end for the filtering assembly which will remain intact during usage.

Referring now to FIGS. 6–9, an alternative embodiment of the embolic filter device 90 is shown which includes an expandable filter assembly 92 with an expandable cage 94. In this particular embodiment, the expandable cage is a modification of the expandable cage 24 shown in FIGS. 1–5. The filter assembly 92 includes the filter member 96 which is utilized to filter the embolic debris in the body vessel and includes a plurality of openings 98 through which the body fluid flows through while the embolic particles remain trapped in the pocket formed by the filter member 96. The filter assembly 92 is also shown attached to a guide wire 100 which has a proximal end (not shown) which extends outside of the patient's body and is manipulated by the physician in order to steer the device into the target area in the patient's vasculature. This particular embodiment 90 is self-expanding, as the other embodiment shown in FIGS. 1–5, and would be kept in a collapsed delivery position through the use of a sheath which would extend over the filter assembly (as is shown in FIG. 3) in order to deliver the device into the target area.

The expandable cage 94 includes a pair of circumferential members 102 and 104 which are connected together by connecting struts 106. This particular embodiment utilizes a single proximal strut 108 and a single distal strut which extends from the second circumferential member 104 to the obturator 112. A distal coil tip 114 extends distally from the obturator 112 and is utilized by the physician to steer the device into the desired body lumen.

The circumferential members 102 and 104 of this particular expandable cage 94 includes only a pair of bending regions 114 and 116 although it is still possible to utilize other bending regions along the circumferential member if desired.

As a result, the use of a single proximal strut 108 minimizes the surface area of struts placed in front of the opening of the filter assembly 92 thus minimizing the chances that emboli could collect on strut areas rather than being forced into the filter member 96. The use of a single distal strut also allows the device to be more flexible in the distal area where flexibility is needed when negotiating tortuous anatomy. It should be appreciated that a single circumferential member could be used in accordance with the present embodiment or additional circumferential members could be utilized to create a longer filtering assembly if desired.

The proximal strut 108 includes one end 118 which is attached to a collar 120 that is rotatably mounted onto the distal end of the guide wire 100. A pair of stop fittings 122 and 124 maintain the collar 120 rotatably mounted to the distal end of the guide wire 100. The other end 126 of the proximal strut 108 is in turn attached to the bending region 114 located on the proximal circumferential member 102. The distal strut 110 includes one end 128 which is attached to the bending region 116 of the second circumferential member 104 with the other end 130 attached to the obturator 112. FIG. 12 shows one particular method for attaching the distal end 130 to the obturator 112. The method of attachment is very similar to the attachment arrangement shown in FIG. 11 in that the distal end 130 is attached to a tubular member 132 having an outside surface 134 and an inner surface 136. A short segment 138 of the guide wire which is attached to the distal coil tip 114 can be adhesively secured or otherwise fastened to the inner surface 136 of the tubular member 132. Likewise, the distal end 130 of the strut 110 is adhesively bonded or otherwise secured to the outer surface 134 of the tubular member 132. The filter member 96 terminates at a distal end 140 which can be bonded both to the outer surface 134 of the tubular member 132 and also to the inner surface of the obturator 112. In this manner, the distal end of the assembly will remain securely fastened to form an integral unit that will remain intact during usage.

Referring now to FIG. 10, an alternative design to the embodiment of FIGS. 6–9 is shown in which a short segment 142 of the guide wire extends through the opening of the expandable cage 94 and extends to the distal end where the distal coil tip 114 is located. In this particular embodiment of the embolic filtering device 90, the short segment 142 of the guide wire extends through the expandable cage 94 and performs substantially the same functions as the embodiment shown in FIG. 5. The tubular member 132 (not shown in FIG. 10) can also extend into the expandable cage 94 to help prevent the filter 96 from tangling on the guide wire segment 142 when the cage 94 is collapsed. The use of a guide wire which extends to the distal most end of the device provides good torqueability to the physician when maneuvering the device in the patient's vasculature. It should also be noted that the expandable cage 94 shown in FIGS. 6–9 could also be permanently affixed to the distal end of the guide wire, rather than being rotatably mounted thereto.

The expandable cage of the present invention can be made in many ways. One particular method of making the cage is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser. The tubing used to make the cage could possible be made of suitable biocompatible material such as spring steel. Elgiloy is another material which could possibly be used to manufacture the cage. Also, very elastic polymers possibly could be used to manufacture the cage.

The strut size is often very small, so the tubing from which the cage is made may have a small diameter. Typically, the tubing has an outer diameter on the order of about 0.020–0.040 inches in the unexpanded condition. Also, the cage can be cut from large diameter tubing. Fittings are attached to both ends of the lased tube to form the final cage geometry. The wall thickness of the tubing is usually about 0.076 mm (0.001–0.006 inches). As can be appreciated, the strut width and/or depth at the bending points will be less. For cages deployed in body lumens, such as PTA applications, the dimensions of the tubing may be correspondingly larger. While it is preferred that the cage be made from laser cut tubing, those skilled in the art will realize that the cage can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The cage can be laser cut much like a stent is laser cut. Details on how the tubing can be cut by a laser are found in U.S. Pat. No. 5,759,192 (Saunders), U.S. Pat. No. 5,780,807 (Saunders) and U.S. Pat. No. 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding cage made in accordance with the present invention.

In one example, the cage of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the cage such that it is super elastic at body temperature. The transformation temperature is at or below body temperature so that the cage is superelastic at body temperature. The cage is usually implanted into the target vessel which is smaller than the diameter of the cage in the expanded position so that the struts of the cage apply a force to the vessel wall to maintain the cage in its expanded position. It should be appreciated that the cage can be made from either superelastic, stress-induced martensite NiTi or shape-memory NiTi.

The cage could also be manufactured by laser cutting a large diameter tubing of nickel-titanium which would create the cage in its expanded position. Thereafter, the formed cage could be placed in its unexpanded position by back-loading the cage into a restraining sheath which will keep the device in the unexpanded position until it is ready for use. If the cage is formed in this manner, there would be no need to heat treat the tubing to achieve the final desired diameter.

This process of forming the cage could be implemented when using superelastic or linear-elastic nickel-titanium.

The struts forming the proximal struts can be made from the same or a different material than the distal struts. In this manner, more or less flexibility for the proximal struts can be obtained. When a different material is utilized for the struts of the proximal struts, the distal struts can be manufactured through the lazing process described above with the proximal struts being formed separately and attached. Suitable fastening means such as adhesive bonding, brazing, soldering, welding and the like can be utilized in order to connect the struts to the distal assembly. Suitable materials for the struts include superelastic materials, such as nickel-titanium, spring steel, Elgiloy, along with polymeric materials which are sufficiently flexible and bendable.

The connecting struts utilized to connect one or more circumferential members together are shown generally as straight segments. However, it is possible to utilize non-linear shapes and sizes which may provide additional flexibility and bendability within the patient's anatomy. Additionally, it is possible to make these connecting struts out of materials which are different from the rest of the expandable cage to further increase flexibility if needed. For example, the connecting strut could be made in an S-shape which may provide additional flexibility in certain curved locations in the patient's anatomy. Moreover, the size and width of the strut could be varied from the remaining strut widths and thicknesses in order to promote additional flexibility. In a similar fashion, the bending regions formed on the circumferential members could also be formed with thinner and narrower strut widths than the remaining elements of the cage in order to enhance flexibility at these bending regions.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050–0.0050 inches. The wall thickness may vary depending on the particular material selected. The material can be made into a cone or similarly sized shape utilizing blow-mold technology or dip technology. The openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the device. Additionally, the filter material can have a "set" put in it much like the "set" used in dilatation balloons to make the filter element rewrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. An embolic filtering device used to capture embolic debris in a body vessel, comprising:
   a guide wire having a proximal end and a distal end; and
   an expandable filter assembly mounted near the distal end of the guide wire, the filter assembly including a self-expanding cage having a proximal circumferential member adapted to move between a collapsed position and an expanded position, the proximal circumferential member including a plurality of bending regions formed therein, a distal circumferential member adapted to move between a collapsed position and an expanded position, the distal circumferential member including a plurality of bending regions formed therein, the proximal circumferential member being connected to the distal circumferential member, a proximal strut attached to the proximal circumferential member, a distal strut attached to the distal circumferential member, and a filter element attached to the self-expanding cage, wherein the bending regions of the proximal circumferential member are connected to and in phase with the bending regions of the distal circumferential member.

2. The filtering device of claim 1, wherein the proximal strut and distal strut are attached to the proximal and distal circumferential members at bending regions.

3. The filtering device of claim 1, further including a plurality of proximal struts attached to bending regions located on the proximal circumferential member.

4. The filtering device of claim 3, further including a plurality of distal struts attached to bending regions located on the distal circumferential member.

5. The filtering device of claim 1, wherein the proximal and distal circumferential members are attached to each other by at least one connecting strut.

6. The filtering device of claim 1, further including a plurality of connecting struts connecting to bending regions formed on the proximal and distal circumferential members.

7. An embolic filtering device used to capture embolic debris in a body vessel, comprising:
   a guide wire having a proximal end and a distal end; and
   an expandable filter assembly mounted near the distal end of the guide wire, the filter assembly including a self-expanding cage having a proximal circumferential member adapted to move between a collapsed position and an expanded position, the proximal circumferential member including a plurality of bending regions formed therein, a distal circumferential member adapted to move between a collapsed position and an expanded position, the distal circumferential member including a plurality of bending regions formed therein, the proximal circumferential member being connected to the distal circumferential member, a plurality of proximal struts attached to the proximal circumferential member, a plurality of distal struts attached to the distal circumferential member, and a filter element attached to the self-expanding cage, wherein the bending regions of the proximal circumferential member are connected to and in phase with the bending regions of the distal circumferential member.

8. The filtering device of claim 7, wherein each of the proximal struts is attached to a bending region on the proximal circumferential member and each of the distal struts is attached to a bending region on the distal circumferential member.

9. The filtering device of claim 7, wherein the proximal and distal circumferential members are attached to each other by at least one connecting strut.

10. The filtering device of claim 7, further including a plurality of connecting struts which connect the proximal circumferential member to the distal circumferential member.

11. The filtering device of claim 7, wherein each connecting member is attached at a bending region on each of the proximal and distal circumferential member.

12. An embolic filtering device used to capture embolic debris in a body vessel, comprising:
a guide wire having a proximal end and a distal end; and
an expandable filter assembly rotatably attached to the distal end of the guide wire, the filter assembly including a self-expanding cage having a proximal circumferential member having a plurality of bending regions formed therein, a distal circumferential member having a plurality of bending regions formed therein, the proximal circumferential member being connected to the distal circumferential member, and a filter element attached to the self-expanding cage, wherein the bending regions of the proximal circumferential member are in phase with the bending regions of the distal circumferential member.

13. The filtering device of claim 12, wherein the self-expanding cage includes a proximal strut having a first end rotatably attached to the distal end of the guide wire and a second end attached to the proximal circumferential member.

14. The filtering device of claim 12, further including a coil tip attached to the filter assembly.

15. The filtering device of claim 14, further including a distal strut having one end attached to the distal circumferential member and a second end coupled to the coil tip.

16. The filtering device of claim 12, wherein each bending region is located about 180 degrees apart from the other on each of the proximal and distal circumferential members.

17. The filtering device of claim 12, wherein the proximal and distal circumferential members are attached to each other by at least one connecting strut.

18. The filtering device of claim 12, wherein the proximal and distal circumferential members are attached to each other at bending regions.

19. An embolic filtering device used to capture embolic debris in a body vessel, comprising:
a guide wire having a proximal end and a distal end; and
an expandable filter assembly mounted near the distal end of the guide wire, the filter assembly including a self-expanding cage having a proximal circumferential member with a plurality of proximal and distal bending regions formed therein, a distal circumferential member with a plurality of proximal and distal bending regions formed therein, the proximal and distal circumferential members being movable between a collapsed position and an expanded position, a proximal strut attached to each of the proximal bending regions of the proximal circumferential member, and a filter element attached to the self-expanding cage, wherein the proximal bending regions of the proximal and distal circumferential members are connected together wherein the bending regions of the proximal circumferential member are in phase with the bending region of the distal circumferential member and the distal bending regions of the proximal and distal circumferential members are connected together.

20. The filtering device of claim 19, wherein the proximal struts each include a first end which is attached to the distal end of the guide wire and a second end attached to the proximal bending region of the proximal circumferential member.

21. The filtering device of claim 19, wherein first ends of the proximal struts are rotatably attached to the guide wire.

22. The filtering device of claim 19, wherein each proximal bending region is located about 180 degrees apart from the other on each of the proximal and distal circumferential members.

23. An embolic filtering device used to capture embolic debris in a body vessel, comprising:
a guide wire having a proximal end and a distal end; and
an expandable filter assembly mounted near the distal end of the guide wire, the filter assembly including a self-expanding cage having a proximal circumferential member with a plurality of proximal U-shaped bending regions and a plurality of distal U-shaped bending regions formed therein, a distal circumferential member with a plurality of proximal U-shaped bending regions and a plurality of distal U-shaped bending regions formed therein, the proximal and distal circumferential members being movable between an collapsed position and an expanded position, and a filter element attached to the self-expanding cage, wherein the proximal U-shaped bending regions of the proximal and distal circumferential members are connected together and in phase with each other.

24. The filtering device of claim 23, wherein the distal U-shaped bending regions of the proximal and distal circumferential members are connected together and in phase with each other.

25. The filtering device of claim 23, wherein each of proximal and distal U-shaped bending regions substantially retains its shaped in both the expanded and collapsed positions.

* * * * *

UNITED STATES PATENT AND TRADEMARK OFFICE
CERTIFICATE OF CORRECTION

| | | |
|---|---|---|
| PATENT NO. | : 7,241,304 B2 | Page 1 of 2 |
| APPLICATION NO. | : 10/027915 | |
| DATED | : July 10, 2007 | |
| INVENTOR(S) | : William J. Boyle et al. | |

It is certified that error appears in the above-identified patent and that said Letters Patent is hereby corrected as shown below:

<u>Title page</u>, OTHER PUBLICATIONS, delete "Dilitation of the Carotid Artery" and insert --Dilatation of the Carotid Artery--.

<u>Title Page 4</u>, U.S. PATENT DOCUMENTS, delete "7,097,834 B1  8/2006  Boyle et al." and insert --7,097,440 B2  8/2006  Papp et al.--.

<u>Column 4</u>,
Line 36, delete "in a outward" and insert --in an outward--.
Line 64, delete "to deployed" and insert --to be deployed--.

<u>Column 8</u>,
Line 57, continue on with "In this manner" (not a new paragraph).

<u>Column 9</u>,
Line 66, delete "fill-length" and insert --full-length--.

<u>Column 12</u>,
Line 9, delete "possible" and insert --possibly--.

<u>Column 13</u>,
Line 24, continue on with "This process of forming" (not a new paragraph).

<u>Column 14</u>,
Line 13, delete "polyolifin" and insert --polyolefin--.

<u>Column 15</u>,
Line 30, delete "claim 7" and insert --claim 10--.

UNITED STATES PATENT AND TRADEMARK OFFICE
CERTIFICATE OF CORRECTION

PATENT NO. : 7,241,304 B2
APPLICATION NO. : 10/027915
DATED : July 10, 2007
INVENTOR(S) : William J. Boyle et al.

It is certified that error appears in the above-identified patent and that said Letters Patent is hereby corrected as shown below:

Column 16,
Line 50, delete "an collapsed" and insert --a collapsed--.

Signed and Sealed this

Thirteenth Day of November, 2007

JON W. DUDAS
*Director of the United States Patent and Trademark Office*